US 8,005,190 B2

(12) United States Patent
Shibuya et al.

(10) Patent No.: US 8,005,190 B2
(45) Date of Patent: Aug. 23, 2011

(54) RADIOTHERAPY APPARATUS CONTROLLER AND IRRADIATION METHOD

(75) Inventors: Osamu Shibuya, Hiroshima (JP); Shuji Kaneko, Hiroshima (JP); Kunio Takahashi, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 132 days.

(21) Appl. No.: 12/549,824

(22) Filed: Aug. 28, 2009

(65) Prior Publication Data

US 2010/0202588 A1   Aug. 12, 2010

(30) Foreign Application Priority Data

Feb. 10, 2009   (JP) .................. 2009-028934

(51) Int. Cl.
*A61N 5/10*   (2006.01)
(52) U.S. Cl. .......................... 378/65; 378/205
(58) Field of Classification Search ............ 378/65, 378/205, 207
See application file for complete search history.

(56) References Cited

U.S. PATENT DOCUMENTS

| | | | |
|---|---|---|---|
| 5,784,431 A | | 7/1998 | Kalend et al. |
| 6,341,172 B1 | | 1/2002 | Xu et al. |
| 7,197,107 B2 * | | 3/2007 | Arai et al. ............... 378/20 |
| 7,453,984 B2 * | | 11/2008 | Chen et al. .............. 378/65 |
| 2003/0058999 A1 * | | 3/2003 | Mitschke et al. ........ 378/207 |

FOREIGN PATENT DOCUMENTS

| | | |
|---|---|---|
| JP | 1-274741 | 11/1989 |
| JP | 10-234715 | 9/1998 |
| JP | 2001-503176 | 3/2001 |
| JP | 2004-97646 | 4/2004 |
| JP | 2006-21046 | 1/2006 |
| JP | 2006-149438 | 6/2006 |
| JP | 2007-502166 | 2/2007 |
| JP | 2007-267972 | 10/2007 |

OTHER PUBLICATIONS

Japanese Office Action issued Jan. 7, 2011 in corresponding Japanese Patent Application No. 2009-028934 w/partial translation.
Japanese Office Action issued Jun. 9, 2011 in corresponding Japanese Patent Application No. 2009-028934 w/partial translation.

* cited by examiner

*Primary Examiner* — Hoon Song
(74) *Attorney, Agent, or Firm* — Wenderoth, Lind & Ponack, L.L.P.

(57) ABSTRACT

A radiotherapy apparatus controller includes: a portal image taking unit; a gantry position collector; a marker position calculator; and a marker position table generator. The portal image taking unit takes a first transmission image, in which a marker member positioned at a predetermined position is shown, by using therapeutic radiation and an imager. The gantry position collector collects a first gantry position at which a gantry is positioned when the first transmission image is taken from a sensor measuring a position at which the gantry is positioned, the gantry supporting the imager and a therapeutic radiation radiating device which radiates the therapeutic radiation. The marker position calculator calculates a first marker position at which the marker member is shown in the first transmission image. The marker position table generator updates a marker position table, which correlates a plurality of gantry positions with a plurality of marker positions, so that the first gantry position corresponds to the first marker position.

18 Claims, 8 Drawing Sheets

RADIOTHERAPY APPARATUS CONTROLLER AND IRRADIATION METHOD

INCORPORATION BY REFERENCE

This application is based upon and claims the benefit of priority from Japanese patent application No. 2009-028934 filed on Feb. 10, 2009, the disclosure of which is incorporated herein in its entirety by reference.

BACKGROUND OF THE INVENTION

1. Field of the Invention

The present invention relates to a radiotherapy apparatus controller and an irradiation method, and more particularly relates to a radiotherapy apparatus and an irradiation method that are used when a tumor area inside a subject is irradiated with a therapeutic radiation.

2. Description of Related Art

Radiotherapy is known in which a patient is treated by irradiating an affected area (tumor) with a therapeutic radiation. As for the radiotherapy, a therapeutic effect is desired to be high. The therapeutic radiation is desired such that a dose of the radiation radiated into normal cells is smaller than a dose of the radiation radiated into cells of the affected area. For this reason, the therapeutic radiation is required to be accurately radiated to the affected area. The radiotherapy apparatus for performing the radiotherapy includes an imager system for imaging a transmission image of the affected area, a therapeutic radiation radiating device for radiating the therapeutic radiation, and a driver for driving the therapeutic radiation radiating device. The radiotherapy apparatus calculates the position of the affected area based on the transmission image and drives the therapeutic radiation radiating device by using the driver such that the therapeutic radiation is radiated to the calculated position.

A supporting structure that supports the therapeutic radiation radiating device and the imager system sags under its own weight and the weight of the therapeutic radiation radiating device. For this reason, when the supporting structure is moved, there is a case that a different visual field deviated from a desirable visual field is projected on the transmission image of the patient. At this time, in a positioning operation of an irradiation target and a positioning accuracy testing, erroneous information is given to a user. It is desired to accurately execute the positioning operation of the irradiation target and the positioning accuracy testing.

Japanese Laid-Open Patent Application JP-A-Heisei 10-234715 (corresponding to U.S. Pat. No. 6,341,172 (B1)) discloses an improved medical imaging system. The medical imaging system is characterized in that this includes an image detector which is configured to receive an image projected by a radiation beam and convert the image into a visual image, the visual image defining a remarkable signal with an upper limit/boundary and a lower limit/boundary, a video detector actively coupled to the image detector, the video detector receiving the visual image and generating a histogram from the visual image, and a video processing circuit, the video processing circuit being configured to automatically identify the upper limit/boundary of the remarkable signal from the histogram.

Japanese Laid-Open Patent Application JP-P 2001-503176A (corresponding to U.S. Pat. No. 5,784,431(A)) discloses an apparatus that can be used to control the radiotherapy apparatus. The apparatus is the apparatus for automatically comparing a portal image and a simulation image. This is provided with a means for digitizing the portal image and the simulation image and respectively generating a digital portal image signal (DPIS) and a digital simulation image signal (DSIS); a processing means for processing the DPIS and the DSIS and generating already-compared DPIS and DSIS; and a means for generating outputs from the already-compared DPIS and DSIS.

Japanese Laid-Open Patent Application JP-P 2006-149438A discloses an irradiation position matching system for supporting a position matching of an irradiation part, which is good in convenience and excellent in reproduction and based on an irradiation plan. The irradiation position matching system is the system for adjusting the position of the irradiation part by using a radiotherapy plan image (DRR: Digital Reconstructed Radiograph) and an irradiation field verification image (LG: lineacgraphy) that is imaged prior to a treatment. This is characterized by including: an image obtaining means for obtaining the DRR, a shape data to create an irradiation field (FOV: Field Of View) and the LG; a pre-processing means for matching the sizes and positions between images of the obtained the DRR and the LG; an edge emphasizing means for emphasizing the edges of the images of the DRR and the LG; an FOV edge removing means for removing an FOV edge in the LG by using the obtained shape data; a binary means for converting the images of the DRR and LG into binary data; a thinning means for thinning the edges of the images of the DPR and LG that are converted into the binary data; a matching means for detecting the gaps of the DPR and LG; and a displaying means for displaying the matching result.

Japanese Laid-Open Patent Application JP-P 2007-267972A discloses an radiotherapy apparatus that can orient an irradiation axis of an X-ray, which is radiated from a therapeutic X-ray generating source, to a predetermined position always located at an irradiation target affected area, in order to irradiate the affected area with the X-ray of a moderate amount and attain a drop in the X-ray irradiation amount to the healthy tissue around the affected area. The radiotherapy apparatus includes: a gantry that can rotate around a first axis passing through an isocenter and can rotate even around a second axis crossing the first axis at the isocenter; an imaging apparatus arranged in the gantry; and a controller. The controller, from a plurality of positions of rotation angles that are defined as the angles around the first axis of the gantry, controls the imaging apparatus to take the images of a marker member, specifies the isocenter specification position based on each of the visual field positions of the images.

Japanese Laid-Open Patent Application JP-P 2006-21046A discloses an radiotherapy apparatus including: an O-shaped gantry; an irradiation head attached and movable to the O-shaped gantry and irradiating a irradiation field of a subject with therapeutic radiation; an X-ray source attached and movable to the O-shaped gantry and irradiating the irradiation field of the subject with diagnostic X-ray; a sensor array attached and movable to the O-shaped gantry and detecting transmitted X-ray which is the diagnostic X-ray transmitted through the subject and outputting as diagnostic image data. The sensor array and the X-ray source move in association with the movement of the irradiation head on the O-shaped gantry.

Japanese Laid-Open Patent Application JP-P 2004-97646A discloses an radiotherapy apparatus including: an irradiation head irradiating a irradiation field of a subject with therapeutic radiation; an X-ray source irradiating the irradiation field of the subject with diagnostic X-ray; a sensor array detecting transmitted X-ray which is the diagnostic X-ray transmitted through the subject and outputting as diagnostic image data. The sensor array moves in association with the movement of the irradiation head on the O-shaped gantry.

SUMMARY OF THE INVENTION

An object of the present invention is to provide a radiotherapy apparatus controller and an irradiation method, which can accurately execute the positioning operation of the irradiation target and the positioning accuracy testing.

In order to achieve an aspect of the present invention, the present invention provides a radiotherapy apparatus controller including: a portal image taking unit configured to take a first transmission image, in which a marker member positioned at a predetermined position is shown, by using therapeutic radiation and an imager; a gantry position collector configured to collect a first gantry position at which a gantry is positioned when the first transmission image is taken from a sensor measuring a position at which the gantry is positioned, the gantry supporting the imager and a therapeutic radiation radiating device which radiates the therapeutic radiation; a marker position calculator configured to calculate a first marker position at which the marker member is shown in the first transmission image; and a marker position table generator configured to update a marker position table, which correlates a plurality of gantry positions with a plurality of marker positions, so that the first gantry position corresponds to the first marker position.

In order to achieve another aspect of the present invention, the present invention provides an irradiation method, including: taking a first transmission image, in which a marker member positioned at a predetermined position is shown, by using therapeutic radiation and an imager; measuring a first gantry position at which a gantry is positioned when the first transmission image is taken, the gantry supporting the imager and a therapeutic radiation radiating device which radiates the therapeutic radiation; calculating a first marker position at which the marker member is shown in the first transmission image; and updating a marker position table, which correlates a plurality of gantry positions with a plurality of marker positions, so that the first gantry position corresponds to the first marker position.

In order to achieve yet another aspect of the present invention, the present invention provides a computer-readable medium including code that, when executed, causes a computer to perform the following: taking a first transmission image, in which a marker member positioned at a predetermined position is shown, by using therapeutic radiation and an imager; collecting a first gantry position at which a gantry is positioned when the first transmission image is taken from a sensor measuring a position at which the gantry is positioned, the gantry supporting the imager and a therapeutic radiation radiating device which radiates the therapeutic radiation; calculating a first marker position at which the marker member is shown in the first transmission image; and updating a marker position table, which correlates a plurality of gantry positions with a plurality of marker positions, so that the first gantry position corresponds to the first marker position.

According to the radiotherapy apparatus controller and the irradiation method according to the present invention, even when the movement of the gantry causes the region projected on the transmission image to be moved, a user can recognize the region projected on the transmission image more accurately, by using its marker position table. For this reason, the user can verify the positional relation between the radiation and the target to which the radiation is radiated, more accurately based on the transmission image.

BRIEF DESCRIPTION OF THE DRAWINGS

The above and other objects, advantages and features of the present invention will be more apparent from the following description of certain preferred embodiments taken in conjunction with the accompanying drawings, in which.

DESCRIPTION OF THE PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposed.

Figure 1:
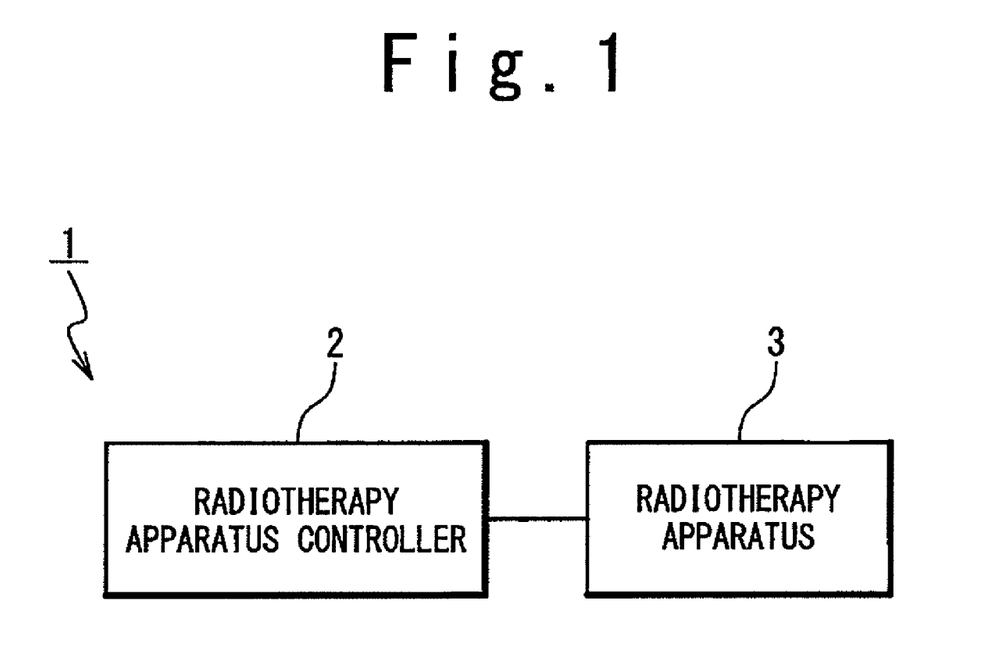
FIG. 1 is a block diagram showing a radiotherapy system according to the embodiment of the present invention.

An embodiment of the radiotherapy apparatus controller according to the present invention will be described below with reference to the drawings. The radiotherapy apparatus controller 2 is applied to a radiotherapy system 1 as shown in FIG. 1. The radiotherapy system 1 includes the radiotherapy apparatus controller and a radiotherapy apparatus 3. The radiotherapy apparatus controller 2 is a computer exemplified as a personal computer. The radiotherapy apparatus controller 2 and the radiotherapy apparatus 3 are connected to each other available for two-way communication.

Figure 2:
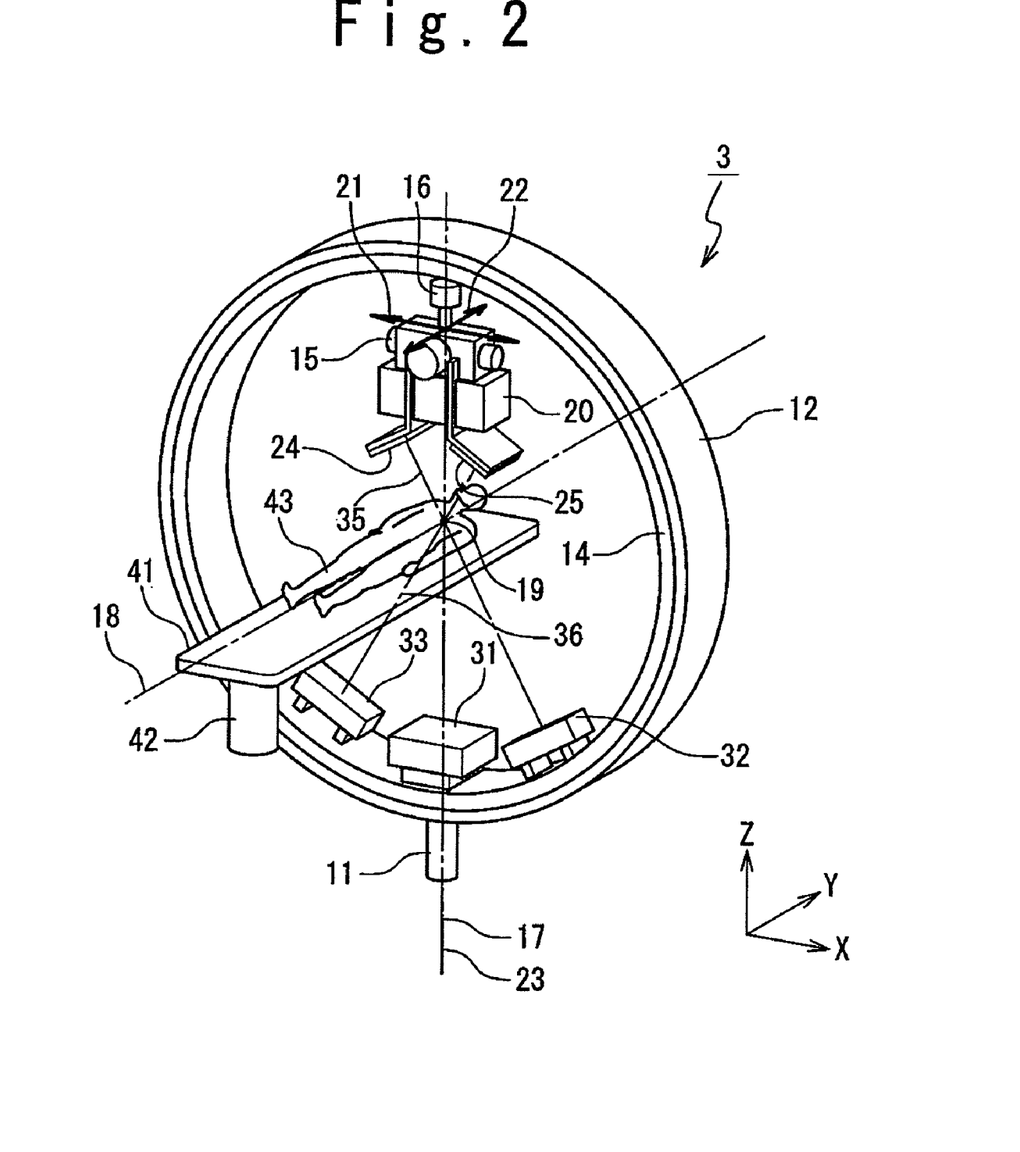
FIG. 2 is a perspective view showing a radiotherapy apparatus according to the embodiment of the present invention.

FIG. 2 shows the radiotherapy apparatus 3. The radiotherapy apparatus 3 includes a rotation driver 11, an O-ring 12, a traveling gantry 14, a head swing mechanism 15 and a therapeutic radiation radiating device 16. The rotation driver 11 supports the O-ring 12 on a base so as to rotate the O-ring 12 around a rotational axis 17. The rotation driver 11 is controlled by the radiotherapy apparatus controller 2 to rotate the O-ring 12 around the rotational axis 17. The rotational axis 17 is parallel to a vertical direction. The rotation driver 11 further measures the rotational angle of the O-ring 12 with respect to the base. The O-ring 12 has a shape of a ring with a rotational axis 18 as an axis, and supports the traveling gantry 14 so as to rotate the traveling gantry 14 around the rotational axis 18. The rotational axis 18 is vertical to the vertical direction and passes through an isocenter 19 included in the rotational axis 17. The rotational axis 18 is further fixed to the O-ring 12. That is, the rotational axis 18 is rotated together with the O-ring 12 around the rotational axis 17. The traveling gantry 14 has a shape of a ring with the rotational axis 18 as a center. The traveling gantry 14 is arranged concentrically with the ring of the O-ring 12. The radiotherapy apparatus 3 further includes a traveling driver that is not shown. The traveling driver is controlled by the radiotherapy apparatus controller 2 so as to rotate the traveling gantry 14 around the rotational axis 18. The traveling driver further measures the traveling angle of the traveling gantry 14 with respect to the O-ring 12.

The head swing mechanism 15 supports the therapeutic radiation radiating device 16 in the traveling gantry 14 so that the therapeutic radiation radiating device 16 is arranged inside the traveling gantry 14. The head swing mechanism 15 has a tilt axis 21 and a pan axis 22. The pan axis 22 is fixed to the traveling gantry 14 and parallel to the rotational axis 18 without crossing the rotational axis 18. The tilt axis 21 is orthogonal to the pan axis 22. The head swing mechanism 15 is controlled by the radiotherapy apparatus controller 2 so as to rotate the therapeutic radiation radiating device 16 around the pan axis 22 and rotate the therapeutic radiation radiating device 16 around the tilt axis 21.

The therapeutic radiation radiating device 16 is controlled by the radiotherapy apparatus controller 2 so as to radiate a therapeutic radiation 23. The therapeutic radiation 23 is substantially radiated along a straight line passing through an intersection of the pan axis 22 and the tilt axis 21. The therapeutic radiation 23 is generated to have a regular magnitude distribution. The therapeutic radiation radiating device 16 includes a multi leaf collimator (MLC) 20. The multi leaf collimator 20 is controlled by the radiotherapy apparatus controller 2 so as to shield apart of the therapeutic radiation 23 and consequently changes the shape of an irradiation field when the therapeutic radiation 23 is radiated to a patient.

The therapeutic radiation 23 is always substantially passed through the isocenter 19, even if the O-ring 12 is rotated by the rotation driver 11 or even if the traveling gantry 14 is rotated by the traveling driver, once the therapeutic radiation radiating device 16 is adjusted to be oriented to the isocenter 19 by the head swing mechanism 15, because the therapeutic radiation radiating device 16 is supported by the traveling gantry 14 as mentioned above. That is, since the traveling and the rotation are carried out, the therapeutic radiation 23 can be radiated from any direction to the isocenter 19.

The radiotherapy apparatus 3 further includes a plurality of imager systems. That is, the radiotherapy apparatus 3 includes diagnostic X-ray sources 24, 25 and sensor arrays 32, 33. The diagnostic X-ray source 24 is supported by the traveling gantry 14. The diagnostic X-ray source 24 is arranged inside the ring of the traveling gantry 14 and arranged at a position at which an angle between a line from the isocenter 19 to the diagnostic X-ray source 24 and a line from the isocenter 19 to the therapeutic radiation radiating device 16 is acute. The diagnostic X-ray source 24 is controlled by the radiotherapy apparatus controller 2 so as to radiate a diagnostic X-ray 35 to the isocenter 19. The diagnostic X-ray 35 is radiated from one point in the diagnostic X-ray source 24, and is a cone beam having a shape of a cone in which its one point serves as an apex. The diagnostic X-ray source 25 is supported by the traveling gantry 14. The diagnostic X-ray source 25 is arranged inside the ring of the traveling gantry 14 and arranged at a position at which an angle between a line from the isocenter 19 to the diagnostic X-ray source 25 and a line from the isocenter 19 to the therapeutic radiation radiating device 16 is acute. The diagnostic X-ray source 25 is controlled by the radiotherapy apparatus controller 2 so as to radiate a diagnostic X-ray 36 to the isocenter 19. The diagnostic X-ray 36 is radiated from one point in the diagnostic X-ray source 25, and is a cone beam having a shape of a cone in which its one point serves as an apex.

The sensor array 32 is supported by the traveling gantry 14. The sensor array 32 receives the diagnostic X-ray 35 which is radiated by the diagnostic X-ray source 24 and transmitted through a subject around the isocenter 19 and then generates the transmission image of the subject. The sensor array 33 is supported by the traveling gantry 14. The sensor array 33 receives the diagnostic X-ray 36 which is radiated by the diagnostic X-ray source 25 and transmitted through the subject around the isocenter 19 and then generates the transmission image of the subject. As the sensor arrays 32, 33, FPD (Flat Panel Detector) and an X-ray II (Image Intensifier) are exemplified.

According to the imager system, the transmission image whose center is located at the isocenter 19 can be generated based on the image signals obtained by the sensor arrays 32, 33.

The radiotherapy apparatus 3 further includes a sensor array 31. The sensor array 31 is arranged such that a line between the sensor array 31 and the therapeutic radiation radiating device 16 passes through the isocenter 19. The sensor array 31 is fixed inside the ring of the traveling gantry 14. The sensor array 31 receives the therapeutic radiation 23 that is radiated by the therapeutic radiation radiating device 16 and transmitted through the subject around the isocenter 19, and then generates the transmission image of the subject. As the sensor array 31, the FPD and the X-ray II are exemplified.

The radiotherapy apparatus 3 further includes a couch 41 and a couch driver 42. The couch 41 is used in order that a patient 43 to be treated by the radiotherapy system 1 is made recumbent. The couch 41 includes a fixing tool that is not shown. The fixing tool fixes the patient to the couch 41 so that the patient does not move. The couch driver 42 supports the couch 41 on the base. The couch driver 42 is controlled by the radiotherapy apparatus controller 2 so as to move the couch 41.

Figure 3:
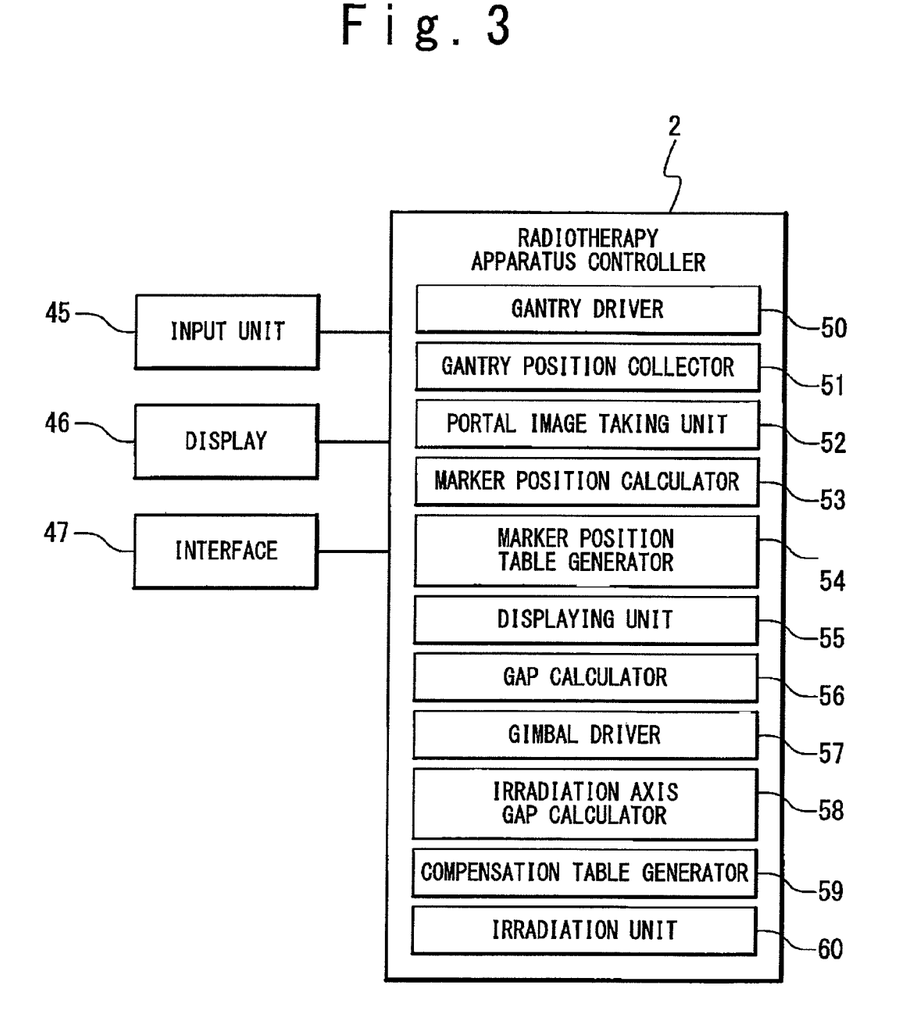
FIG. 3 is a block diagram showing a radiotherapy apparatus controller according to the embodiment of the present invention.

FIG. 3 shows the radiotherapy apparatus controller 2. The radiotherapy apparatus controller 2 includes a CPU and a storage unit, which are not shown, and further includes an input unit 45, a display 46 and an interface 47. The CPU executes a computer program installed in the radiotherapy apparatus controller 2 and controls the storage unit, the input unit 45, the display 46 and the interface 47. The storage unit records the computer program and transiently records the information created by the CPU.

The input unit 45, when operated by the user, creates the information and outputs the information to the CPU. As the input unit, a keyboard is exemplified. The display 46 displays the image created by the CPU. The interface 47 outputs the information, which is created by an external unit connected to the radiotherapy apparatus controller 2, to the CPU and outputs the information created by the CPU to the external unit. The external unit includes the rotation driver 11, the traveling driver, the head swing mechanism 15, the therapeutic radiation radiating device 16, the multi leaf collimator 20, the imager system (the diagnostic X-ray sources 24, 25 and the sensor arrays 31, 32 and 33) and the couch driver 42, in the radiotherapy apparatus 3.

The computer program includes a gantry driver 50, a gantry position collector 51, a portal image taking unit 52, a marker position calculator 53, a marker position table generator 54, a displaying unit 55, a gap calculator 56, a gimbal driver 57, an irradiation axis gap calculator 58, a compensation table generator 59 and an irradiation unit 60.

The gantry driver 50 uses the rotation driver 11 and rotates the O-ring 12 around the rotational axis 17. Thus, the O-ring 12 is positioned at an O-ring rotation angle inputted through the input unit 45. The gantry driver 50 further uses the traveling driver in the radiotherapy apparatus 3 and rotates the traveling gantry 14 around the rotational axis 18. Hence, the traveling gantry 14 is positioned at a gantry traveling angle inputted through the input unit 45.

The gantry position collector 51 collects a gantry position at which the traveling gantry 14 is positioned, from the radiotherapy apparatus 3. The gantry position indicates a rotation angle and a traveling angle. That is, the gantry position collector 51 collects its rotation angle from the rotation driver 11 and collects its traveling angle from the traveling driver in the radiotherapy apparatus 3.

The portal image taking unit 52, when the therapeutic radiation 23 is radiated from the therapeutic radiation radiating device 16, uses the sensor array 31 and images the transmission image of the subject arranged around the isocenter 19.

The marker position calculator 53 executes the image processing to the transmission image taken (imaged) by the portal image taking unit 52 and consequently calculates a marker position.

The marker position table generator 54 records the marker position table in the storage unit so that it can be read from a different computer program. The marker position table generator 54 updates the marker position table based on the gantry position collected by the gantry position collector 51 and the marker position calculated by the marker position calculator 53.

The displaying unit 55 generates a display image based on the transmission image taken by the portal image taking unit 52, the gantry position collected by the gantry position collector 51, and the marker position table generated by the marker position table generator 54, and displays the display image on the display 46.

The gap calculator 56 calculates a gap amount, base on the transmission image taken by the portal image taking unit 52, the gantry position collected by the gantry position collector 51, and the marker position table generated by the marker position table generator 54.

The gimbal driver 57 refers to a control table recorded in the storage unit and calculates a control amount based on the gap amount inputted through the input unit 45. Or, the gimbal driver 57 calculates the control amount base on the transmission image taken by the portal image taking unit 52 and a compensation table generated by the compensation table generator 59. The gimbal driver 57 drives the therapeutic radiation radiating device 16 by using the head swing mechanism 15 based on the calculated control amount.

The irradiation axis gap calculator 58 calculates an irradiation axis gap amount based on the transmission image taken by the portal image taking unit 52.

The compensation table generator 59 generates the compensation table based on the gantry position collected by the gantry position collector 51, the control amount calculated by the gimbal driver 57, and the irradiation axis gap amount calculated by the irradiation axis gap calculator 58.

The irradiation unit 60 uses the rotation driver 11, rotates the O-ring 12 around the rotational axis 17 and positions the O-ring 12 at the rotation angle indicated by a treatment plan inputted to the radiotherapy apparatus controller 2. The irradiation unit 60 further uses the traveling driver in the radiotherapy apparatus 3, rotates the traveling gantry 14 around the rotational axis 18 and positions the traveling gantry 14 at the traveling angle indicated by the treatment plan. The irradiation unit 60 further drives the therapeutic radiation radiating device 16 by using the head swing mechanism 15 so that the therapeutic radiation 23 is transmitted through the affected area of the patient 43, based on the gap amount calculated by the gap calculator 56. The irradiation unit 60 further controls the shape of the irradiation field of the therapeutic radiation 23 by using the multi leaf collimator 20 so that the exposure amount of the therapeutic radiation 23 which is radiated to a risk portion differing from the affected area of the patient 43 is reduced, based on the transmission image taken by the portal image taking unit 52. The irradiation unit 60, after driving the head swing mechanism 15 and the multi leaf collimator 20, uses the therapeutic radiation radiating device 16 and radiates the therapeutic radiation 23.

Figure 4:
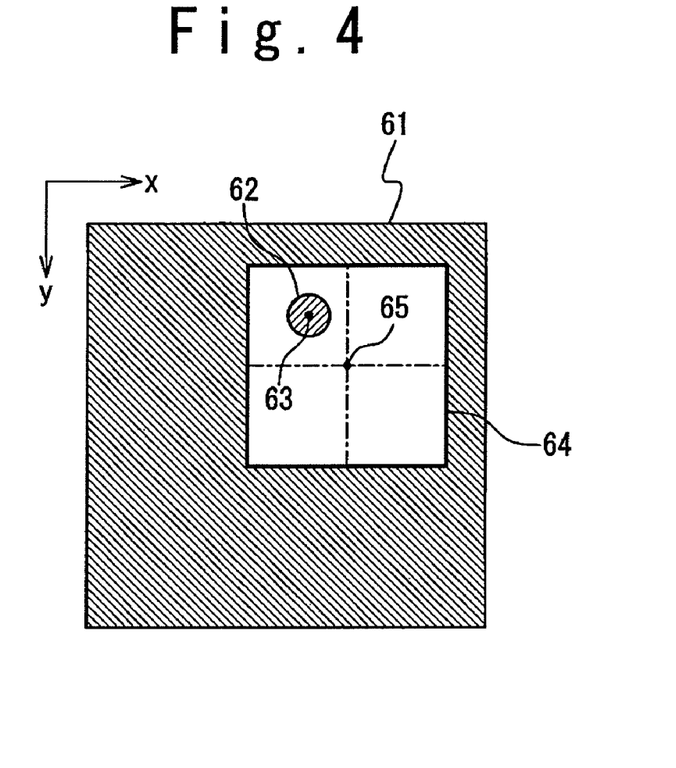
FIG. 4 is a view showing a transmission image taken when a marker member is positioned at an isocenter according to the embodiment of the present invention.

FIG. 4 shows the transmission image taken by the portal image taking unit 52, when a marker member is positioned at the isocenter 19. As the marker member, a metallic ball is exemplified. A marker member FIG. 62 is projected on its transmission image 61. The shape of the marker member FIG. 62 corresponds to the shape of the marker member, and a marker position 63 at which the marker member FIG. 62 is projected on the transmission image 61 corresponds to a position at which the marker member is positioned. Moreover, an irradiation field FIG. 64 is projected on the transmission image 61. The shape of the irradiation field FIG. 64 corresponds to the shape of the irradiation field of the therapeutic radiation 23, and an irradiation axis position 65 at which the irradiation field FIG. 64 is projected on the transmission image 61 corresponds to the irradiation axis of the therapeutic radiation 23.

At this time, the marker position table generator 54 executes the image processing to the transmission image 61 and consequently calculates the marker position 63 of the marker member FIG. 62. The marker position 63 indicates an x-coordinate and a y-coordinate.

Figure 5:
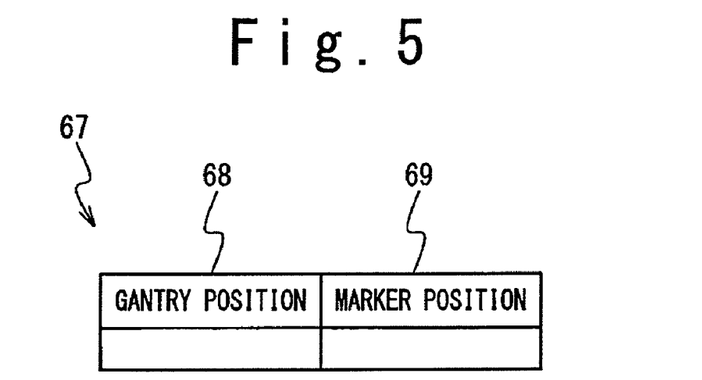
FIG. 5 is a view showing a marker position table according to the embodiment of the present invention.

FIG. 5 shows the marker position table generated by the marker position table generator 54. In its marker position table 67, a gantry position set 68 is correlated with a marker position set 69. That is, any element in the gantry position set 68 correlates to one element in the marker position set 69. Each element in the gantry position set 68 indicates the position of the traveling gantry 14 and indicates the combination of the rotation angle and the traveling angle. Each element in the marker position set 69 indicates the position of the point on the transmission image taken by the portal image taking unit 52 and indicates the combination of the x-coordinate and the y-coordinate.

That is, when the sensor array 31 is used to take (image) the transmission image of the marker member arranged at the isocenter 19, the gantry position collector 51 collects the gantry position at which the traveling gantry 14 is positioned when the transmission image is taken. Then, the marker position table generator 54 executes the image processing to the transmission image and calculates the marker position of the marker member figure on which the marker member is projected. The marker position table generator 54 updates the marker position table 67 so that the collected gantry position corresponds to the calculated marker position. That is, the element of the marker position set 69 indicates the position at which the subject arranged at the isocenter 19 is projected, on the transmission image taken when the traveling gantry 14 is positioned at the gantry position, which corresponds to the element, in the gantry position set 68.

The marker position table generator 54 further calculates the marker position corresponding to the gantry position that indicates the position of the traveling gantry 14 at which the transmission image is not taken; and updates the marker position table 67 so that the gantry position corresponds to the calculated marker position. That is, an x-coordinate X_G0R0 and a y-coordinate Y_G0R0, which are indicated by the marker position corresponding to the gantry position defined by a rotation angle R0 and a traveling angle G0, are represented by the following equation:

$$X\_G0R0 = X\_G0R1 + \frac{X\_G0R2 - X\_G0R1}{R2 - R1} \times (R0 - R1) \quad \text{[Equation 1]}$$

$$Y\_G0R0 = Y\_G0R1 + \frac{Y\_G0R2 - Y\_G0R1}{R2 - R1} \times (R0 - R1) \quad \text{[Equation 2]}$$

Here, the rotation angle R1 and the traveling angle G1 indicate the position of the traveling gantry 14 when the transmission image is taken. The rotation angle R2 and the traveling angle G2 indicate the different position of the traveling gantry 14 when the different transmission image is taken. The rotation angle R1, the rotation angle R2, the traveling angle G1 and the traveling angle G2 satisfy the following equation:

$$G1 \leq G0 \leq G2$$

$$R1 \leq R0 \leq R2$$

Moreover, the x-coordinate X_G0R1 is represented by the following equation:

$$X\_G0R1 = X\_G1R1 + \frac{X\_G2R1 - X\_G1R1}{G2 - G1} \times (G0 - G1) \quad \text{[Equation 3]}$$

The x-coordinate X_G0R2 is represented by the following equation:

$$X\_G0R2 = X\_G1R2 + \frac{X\_G2R2 - X\_G1R2}{G2 - G1} \times (G0 - G1) \quad \text{[Equation 4]}$$

The y-coordinate Y_G0R1 is represented by the following equation:

$$Y\_G0R1 = Y\_G1R1 + \frac{Y\_G2R1 - Y\_G1R1}{G2 - G1} \times (G0 - G1) \quad \text{[Equation 5]}$$

The y-coordinate Y_G0R2 is represented by the following equation:

$$Y\_G0R2 = Y\_G1R2 + \frac{Y\_G2R2 - Y\_G1R2}{G2 - G1} \times (G0 - G1) \quad \text{[Equation 6]}$$

The x-coordinate X_G1R1 and the y-coordinate Y_G1R1 indicate the position of the marker member figure projected on the transmission image that is imaged when the traveling gantry 14 is positioned at the gantry position defined by the rotation angle R1 and the traveling angle G1. The x-coordinate X_G2R2 and the y-coordinate Y_G2R2 indicate the position of the marker member figure projected on the transmission image that is imaged when the traveling gantry 14 is positioned at the gantry position defined by the rotation angle R2 and the traveling angle G2.

Figure 6:
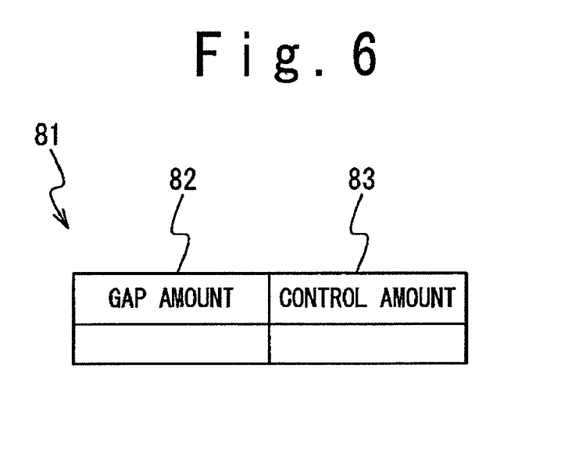
FIG. 6 is a view showing a control table according to the embodiment of the present invention.

FIG. 6 shows the control table that the gimbal driver 57 refers to. The control table 81 correlates a gap amount set 82 with a control amount set 83. That is, any element in the gap amount set 82 corresponds to one element in the control amount set 83. Each element in the gap amount set 82 indicates the gap amount between the two points on the transmission image taken by the portal image taking unit 52 and indicates the combination of an X-component and a y-component. Each element in the control amount set 83 indicates the control value to control the head swing mechanism 15 and indicates the combination of a pan control amount and a tilt control amount.

At this time, when the gap amount is inputted through the input unit 45, the gimbal driver 57 refers to the control table 81 and calculates the control amount corresponding to the inputted gap amount from the control amount set 83. The gimbal driver 57 then outputs the calculated control amount to the head swing mechanism 15 and consequently drives the therapeutic radiation radiating device 16.

Figure 7:
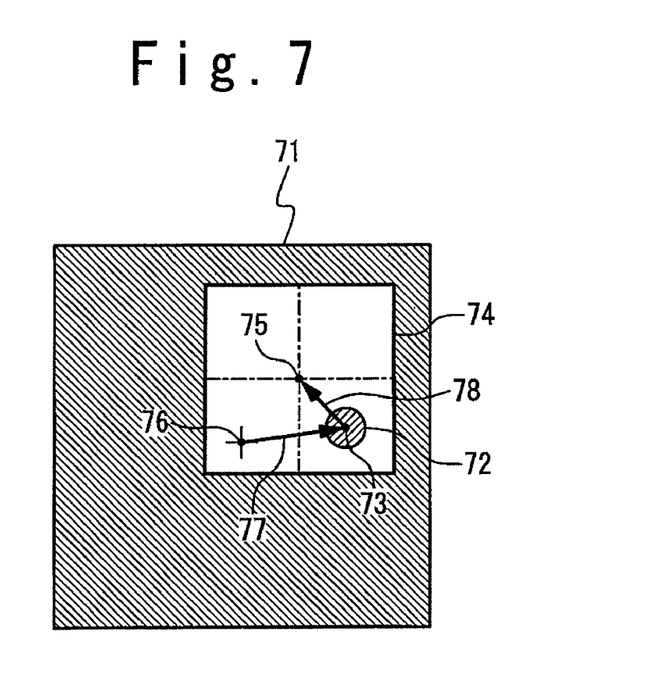
FIG. 7 is a view showing the transmission image taken when the marker member is positioned at a position different from the isocenter according to the embodiment of the present invention.

FIG. 7 shows the transmission image taken by the portal image taking unit 52, when the marker member is arranged at the position slightly different from the isocenter 19. A marker member FIG. 72 is projected on the transmission image 71. The shape of the marker member FIG. 72 corresponds to the shape of the marker member. A marker position 73 at which the marker member FIG. 72 is projected on the transmission image 71 corresponds to the position at which the marker member is positioned. An irradiation field FIG. 74 is further projected on the transmission image 71. The shape of the irradiation field FIG. 74 corresponds to the shape of the irradiation field of the therapeutic radiation 23. An irradiation axis position 75 at which the irradiation field FIG. 74 is projected on the transmission image 71 corresponds to the irradiation axis of the therapeutic radiation 23.

At this time, the gap calculator 56 firstly collects the gantry position at which the traveling gantry 14 is positioned when the transmission image 71 is taken, and refers to the marker position table 67 and calculates an isocenter position 76, which corresponds to the collected gantry position, in the marker position set 69. Next, the gap calculator 56 executes image processing to the transmission image 71 and consequently calculates a gap amount 77 between the isocenter position 76 and the marker position 73. The gap amount 77 indicates the combination of the x-component and the y-component.

The gimbal driver 57 drives the therapeutic radiation radiating device 16 so that the irradiation axis of the therapeutic radiation 23 passes through the marker member based on the gap amount calculated by the gap calculator 56. That is, the gimbal driver 57 refers to the control table 81 and calculates the control amount corresponding to the calculated gap amount from the control amount set 83. Then, the gimbal driver 57 outputs the calculated control amount to the head swing mechanism 15 and consequently drives the therapeutic radiation radiating device 16.

The irradiation axis gap calculator 58 calculates the irradiation axis gap amount based on the transmission image taken after the therapeutic radiation radiating device 16 is driven by the gimbal driver 57. That is, when the transmission image is the transmission image 71, the irradiation axis gap calculator 58 executes image processing to the transmission image 71 and consequently calculates an irradiation axis gap amount 78 that is the gap amount between the marker position 73 and the irradiation axis position 75. The irradiation axis gap amount 78 indicates the combination of the x-component and the y-component.

Figure 8:
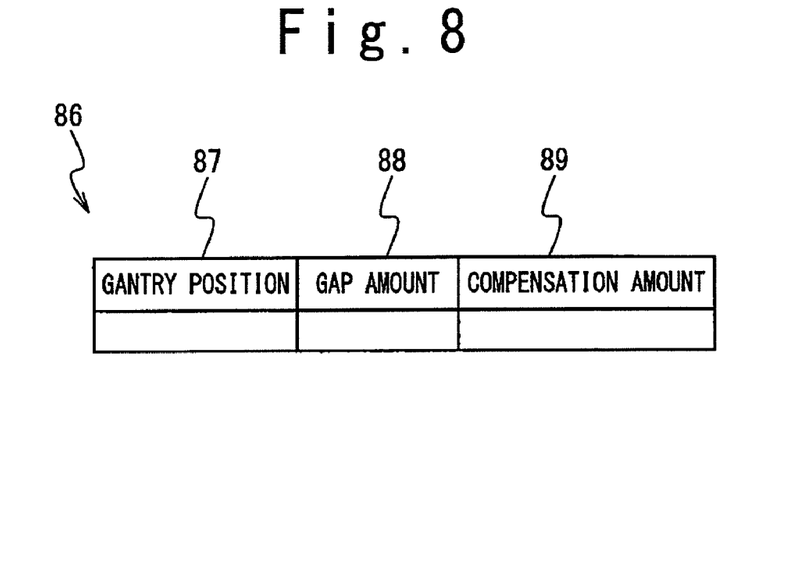
FIG. 8 is a view showing a compensation table according to the embodiment of the present invention.

FIG. 8 shows the compensation table generated by the compensation table generator 59. The compensation table 86 correlates a gantry position set 87 and a gap amount set 88 with a compensation amount set 89. That is, the combination of any element in the gantry position set 87 and any element in the gap amount set 87 corresponds to one element in the compensation amount set 89. Each element in the gantry position set 87 indicates the position of the traveling gantry 14 and indicates the combination of the rotation angle and the traveling angle. Each element in the gap amount set 88 indicates the gap amount between the isocenter position and the marker position and indicates the combination of the x-component and the y-component. Each element in the compensation amount set 89 indicates the compensation amount to compensate the control amount to control the head swing mechanism 15 and indicates the combination of the pan compensation amount and the tilt compensation amount.

When the compensation table 86 is prepared, the gimbal driver 57 uses the control amount compensated based on the compensation table 86 and controls the head swing mechanism 15. That is, the gimbal driver 57 firstly refers to the control table 81 and calculates the control amount, which corresponds to the gap amount calculated by the gap calculator 56, from the control amount set 83. The gimbal driver 57 collects the gantry position at which the traveling gantry 14 is positioned when the transmission image used to calculate the gap amount is taken. The gimbal driver 57 refers to the compensation table 86 and calculates the compensation amount, which corresponds to the gantry position and the gap amount, from the compensation amount set 89. The gimbal driver 57 further compensates the calculated control amount to a post-compensation control amount based on the calculated compensation amount. The post-compensation control amount indicates the combination of the pan control amount and the tilt control amount. The pan control amount of the post-compensation control amount indicates a value in which the pan compensation amount of the compensation amount is added to the pan control amount of the control amount. The tilt control amount of the post-compensation control amount indicates a value in which the tilt compensation amount of the compensation amount is added to the tilt control amount of the control amount. The gimbal driver 57 next outputs the post-compensation control amount to the head swing mechanism 15 and consequently drives the therapeutic radiation radiating device 16.

Figure 9:
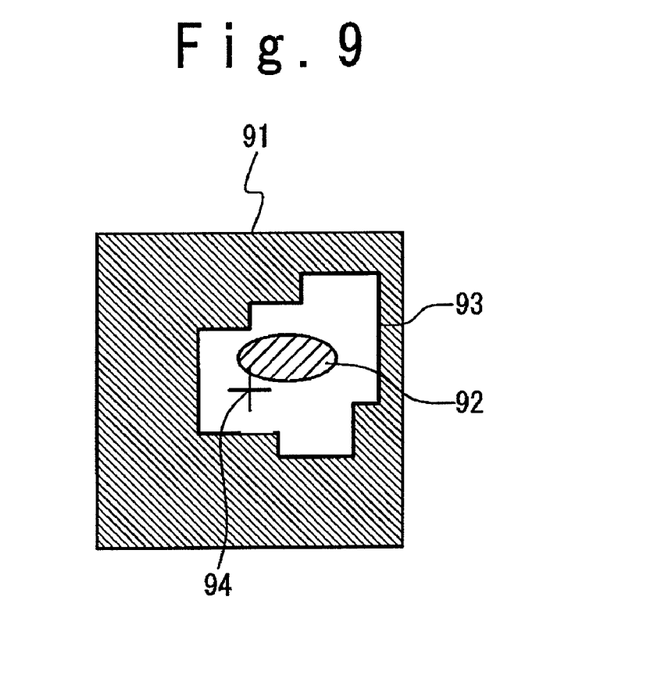
FIG. 9 is a view showing a display screen displayed on a display according to the embodiment of the present invention.

FIG. 9 shows the display image generated by the displaying unit 55. The transmission image taken by the portal image taking unit 52 and an isocenter position FIG. 94 are projected on its display image 91. That is, an affected area FIG. 92 is projected on the display image 91. The shape of the affected area FIG. 92 corresponds to the shape of the affected area of the patient 43. The position at which the affected area FIG. 92 is projected on the display image 91 corresponds to the position at which the affected area is placed. An irradiation field FIG. 93 is further projected on the display image 91. The shape of the irradiation field FIG. 93 corresponds to the shape of the irradiation field of the therapeutic radiation 23. The position at which the irradiation field FIG. 93 is projected on the display image 91 corresponds to the position of the irradiation axis of the therapeutic radiation 23. The isocenter position FIG. 94 is projected on the display image 91. The position at which the isocenter position FIG. 94 is projected on the display image 91 corresponds to the position of the isocenter 19.

That is, the displaying unit 55 collects the gantry position at which the traveling gantry 14 is positioned when the transmission image taken by the portal image taking unit 52 is imaged, refers to the marker position table 67 and calculates the isocenter position, which corresponds to the collected gantry position, in the marker position set 69. The displaying unit 55 generates the display image 91 by overlapping the isocenter position FIG. 94 and the transmission image so that the isocenter position FIG. 94 is projected at the calculated isocenter position in the transmission image, and displays the display image 91 on the display 46.

The embodiment of the irradiation method according to the present invention is executed by the radiotherapy system 1 and includes an operation, for preparing the marker position table, an operation for preparing the compensation table and an operation for carrying out the radiotherapy.

In the operation for preparing the marker position table, the user firstly arranges the marker member at the isocenter 19. The radiotherapy apparatus controller 2 collects the gantry position at which the traveling gantry 14 is positioned, uses the therapeutic radiation radiating device 16 to radiate the therapeutic radiation 23, and uses the sensor array 31 to image the transmission image 61. Next, the radiotherapy apparatus controller 2 executes image processing to the transmission image 61 to calculate the marker position of the marker member figure on which the marker member is projected. Next, the radiotherapy apparatus controller 2 updates the marker position table 67 such that the collected gantry position corresponds to the calculated marker position.

The radiotherapy apparatus controller 2 calculates the marker position similarly, each time the O-ring 12 is positioned at a plurality of predetermined rotation angles by the user and each time the traveling gantry 14 is positioned at a plurality of predetermined traveling angles, and updates the marker position table 67.

The marker position table generator 54 further calculates the marker position corresponding to the gantry position that indicates the position of the traveling gantry 14 in which the transmission image is not imaged, and updates the marker position table 67 so that the gantry position corresponds to the calculated marker position.

In the operation for preparing the compensation table, the user firstly fixes the marker member at the position slightly different from (away from) the isocenter 19. Next, the user operates the radiotherapy apparatus controller 2 to drive the head swing mechanism 15 so that the irradiation axis of the therapeutic radiation 23 passes through the marker member. The radiotherapy apparatus controller 2 collects the gantry position at which the traveling gantry 14 is positioned, uses the therapeutic radiation radiating device 16 to radiate the therapeutic radiation 23, and uses the sensor array 31 to take the transmission image 71. The radiotherapy apparatus controller 2 refers to the marker position table 67 to calculate the isocenter position 76, which corresponds to the collected gantry position, in the marker position set 69. Next, the radiotherapy apparatus controller 2 executes image processing to the transmission image 71, thereby calculating the gap amount 77 between the isocenter position 76 and the marker position 73. The radiotherapy apparatus controller 2 updates the compensation table 86 based on the gap amount 77.

The radiotherapy apparatus controller 2 calculates the gap amount 77 similarly, each time the O-ring 12 is positioned at the plurality of predetermined rotation angles by the user and each time the traveling gantry 14 is positioned at the plurality of predetermined traveling angles, and updates the marker position table 67 based on the gap amount 77.

In the operation for carrying out the radiotherapy, the user firstly fixes the patient 43 to the couch 41 in the radiotherapy apparatus 3. The user further moves the couch 41 so that the affected area of the patient 43 is positioned to substantially overlap with the isocenter 19. The user uses the diagnostic X-ray sources and sensor arrays in the radiotherapy apparatus 3 and radiates the diagnostic X-ray to the patient and images the transmission image of the affected area of the patient. The user moves the couch 41 so that the affected area of the patient 43 is positioned to overlap with the isocenter 19 based on the transmission image.

The radiotherapy apparatus controller 2, after the affected area of the patient is positioned at the isocenter 19, positions the traveling gantry 14 at the gantry position indicated by the treatment plan, and uses the therapeutic radiation radiating device 16 to radiate the therapeutic radiation 23, and uses the sensor array 31 to image the transmission image. The radiotherapy apparatus controller 2 refers to the marker position table 67 to calculate the isocenter position 76, which corresponds to the gantry position, in the marker position set 69. The radiotherapy apparatus controller 2 overlaps the isocenter position FIG. 94 and the transmission image such that the isocenter position FIG. 94 is projected at the calculated isocenter position in the transmission image, thereby generating the display image 91. Then, the radiotherapy apparatus controller 2 displays the display image 91 on the display 46.

The radiotherapy apparatus controller 2 controls the head swing mechanism 15 based on the transmission image, the control table 81 and the compensation table 86 such that the irradiation axis of the therapeutic radiation 23 passes through the affected area. The radiotherapy apparatus controller 2, after the affected area of the patient is positioned such that the therapeutic radiation 23 is radiated to the affected area of the patient, until the dose of the therapeutic radiation 23 radiated to the affected area of the patient reaches the dose of the treatment plan, uses the therapeutic radiation radiating device 16 to radiate the therapeutic radiation 23.

According to these operations, even when the position at which the isocenter 19 is projected on the transmission image is moved based on the traveling gantry 14 is moved, the radiotherapy apparatus controller 2 can accurately recognize the region projected on the transmission image. For this reason, the user can recognize the positional relation between the therapeutic radiation 23 and the affected area of the patient 43 accurately based on the transmission image, and the therapeutic radiation 23 can be radiated accurately to the desired position.

Figure 10:
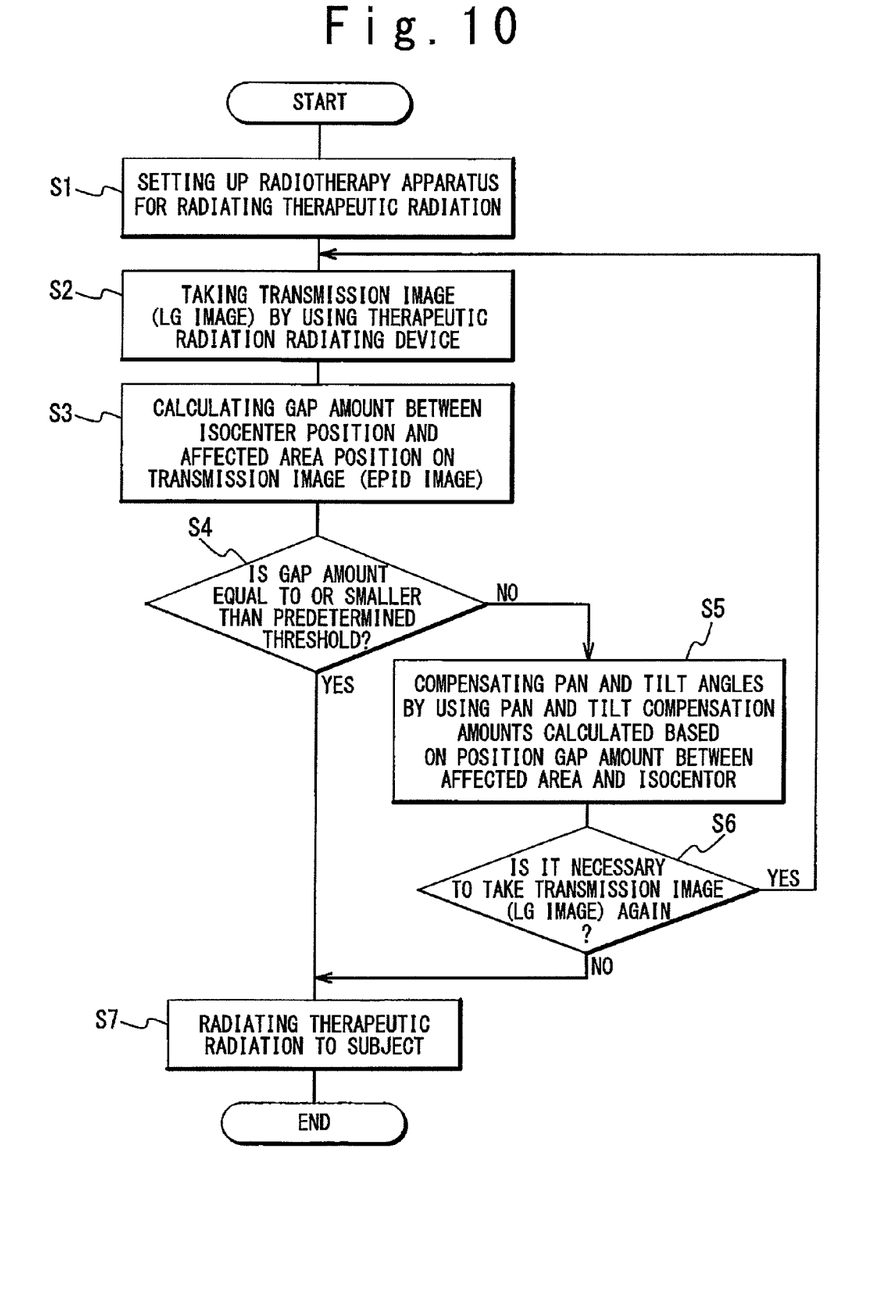
FIG. 10 is a flowchart showing the operations of the radiotherapy according to the embodiment of the present invention.

The operation for carrying out the radiotherapy can be replaced with other operation for carrying out the radiotherapy. FIG. 10 shows the replaceable operation. In this operation, the user firstly fixes the patient 43 to the couch 41 in the radiotherapy apparatus 3. The user further moves the couch 41 so that the affected area of the patient 43 is positioned to substantially overlap with the isocenter 19. The user uses the diagnostic X-ray sources and sensor arrays in the radiotherapy apparatus 3 and radiates the diagnostic X-rays to the patient and then images the transmission image of the affected area of the patient. The user moves the couch 41 so that the affected area of the patient 43 is positioned to overlap with the isocenter 19 based on the transmission image. The radiotherapy apparatus controller 2, after the affected area of the patient is positioned at the isocenter 19, positions the traveling gantry 14 at the gantry position indicated by the treatment plan (Step S1).

The radiotherapy apparatus controller 2 uses the therapeutic radiation radiating device 16 to radiate the therapeutic radiation 23, and uses the sensor array 31 to take the transmission image (Step S2). The radiotherapy apparatus controller 2 refers to the marker position table 67 to calculate the isocenter position, which corresponds to the gantry position, in the marker position set 69. The radiotherapy apparatus controller 2 executes image processing to the transmission image, thereby calculating the gap amount between the isocenter position and the position on which the affected area is projected (Step S3).

The radiotherapy apparatus controller 2, when the gap amount is larger than a predetermined threshold (Step S4, NO), refers to the control table 81 to calculate the control amount, which corresponds to the calculated gap amount, from the control amount set 83. Then, the radiotherapy apparatus controller 2 outputs the calculated control amount to the head swing mechanism 15 to drive the therapeutic radiation radiating device 16 (Step S5). If the therapeutic radiation radiating device 16 is not positioned to radiate the therapeutic radiation 23 to the affected area (Step S6, YES), the radiotherapy apparatus controller 2 executes the steps S2 to S4 again.

If the therapeutic radiation radiating device 16 is positioned to radiate the therapeutic radiation 23 to the affected area (Step S6, NO), or if the calculated gap amount is equal to or smaller than the predetermined threshold (Step S4, YES), until the dose of the therapeutic radiation 23 radiated to the affected area of the patient 43 reaches the dose of the treatment plan, the radiotherapy apparatus controller 2 uses the therapeutic radiation radiating device 16 to radiate the therapeutic radiation 23 (Step S7).

According to these operations, similarly to the foregoing operations, even when the position at which the isocenter 19 is projected on the transmission image is moved based on the movement of the traveling gantry 14, the radiotherapy apparatus controller 2 can control the therapeutic radiation radiating device 16 to radiate the therapeutic radiation 23 accurately to the desired position. According to such operations, it is not necessary for the radiotherapy apparatus controller 2 to execute the operation for preparing the compensation table 86, which is preferable because the operation necessary prior to the radiotherapy is reduced.

Figure 11:
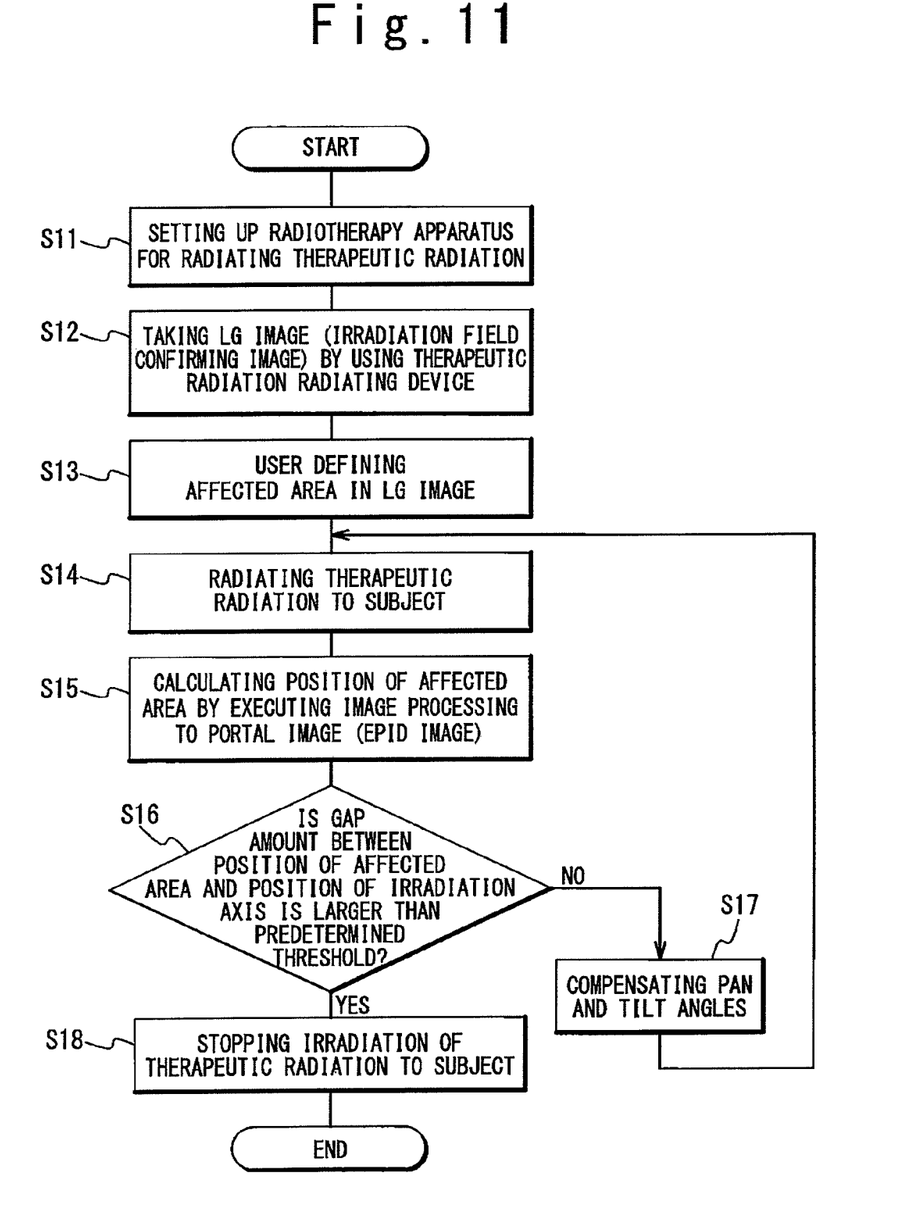
FIG. 11 is a flowchart showing the operations of a moving body tracking radiation according to the embodiment of the present invention.

Incidentally, the operation for carrying out the radiotherapy can be replaced with an operation for carrying out the moving body tracking irradiation in which the tracking operation and the irradiating operation are repeated, when the affected area of the patient 43 is moved correspondingly to the motion of the patient that is exemplified as a respiration and a heartbeat.

In the operation for carrying out the moving body tracking irradiation, as shown in FIG. 11, the user firstly fixes the patient 43 to the couch 41 of the radiotherapy apparatus 3. The user further moves the couch 41 so that the affected area of the patient 43 is positioned to substantially overlap with the isocenter 19. The user uses the diagnostic X-ray sources and sensor arrays in the radiotherapy apparatus 3 and radiates the diagnostic X-rays to the patient and then images the transmission image of the patient 43. The user moves the couch 41 so that the affected area of the patient 43 is positioned to overlap with the isocenter 19 based on the transmission image. After the affected area of the patient is positioned at the isocenter 19, the radiotherapy apparatus controller 2 positions the traveling gantry 14 at the gantry position indicated by the treatment plan (Step S11).

The radiotherapy apparatus controller 2 uses the therapeutic radiation radiating device 16 to radiate the therapeutic radiation 23, and uses the sensor array 31 to take the transmission image (Step S12). The user extracts the image of the affected area from the transmission image and consequently defines the image of the affected area (Step S13).

The radiotherapy apparatus controller 2 uses the therapeutic radiation radiating device 16 to radiate the therapeutic radiation 23 (Step S14), uses the sensor array 31 to take the transmission image, and executes image processing to the transmission image. Thus, the position at which the affected area defined by the user is projected is calculated (Step S15). The radiotherapy apparatus controller 2 further executes image processing to the transmission image, thereby calculating the gap amount between the position at which the affected area is projected and the position at which the isocenter 19 is projected, and further calculating the irradiation axis gap amount that implies the gap amount between the position at which the affected area is projected and the position of the irradiation axis of the therapeutic radiation 23 (Step S16).

If the irradiation axis gap amount is smaller than a predetermined threshold (Step S16, NO), the radiotherapy apparatus controller 2 refers to the control table 81 to calculate the control amount corresponding to the calculated gap amount from the control amount set 83. The radiotherapy apparatus controller 2 collects the gantry position at which the traveling gantry 14 is positioned when the transmission image used to calculate the gap amount is imaged. The radiotherapy apparatus controller 2 refers to the compensation table 86 to calculate the compensation amount, which corresponds to the gantry position and the gap amount, from the compensation amount set 89. The radiotherapy apparatus controller 2 further compensates the calculated control amount to the post-compensation control amount based on the calculated compensation amount. Next, the radiotherapy apparatus controller 2 outputs the post-compensation control amount to the head swing mechanism 15 to drive the therapeutic radiation radiating device 16 (Step S17). After the therapeutic radiation radiating device 16 is driven, the radiotherapy apparatus controller 2 executes the steps S14 to S16 repeatedly. As this repetition cycle, about 100 ms (millisecond) is exemplified.

If the irradiation axis gap amount is larger than the predetermined threshold (Step S16, YES), the radiotherapy apparatus controller 2 stops the operation for carrying out the radiotherapy (Step S18).

That is, such operations can be applied to the moving body tracking operation. According to such operations, similarly to the foregoing operations, even when the movement of the traveling gantry 14 results in the movement of the position at which the isocenter 19 is projected on the transmission image, the radiotherapy apparatus controller 2 can control the therapeutic radiation radiating device 16 to radiate the therapeutic radiation 23 accurately to the desired position.

It is apparent that the present invention is not limited to the above embodiment, but may be modified and changed without departing from the scope and spirit of the invention.

Although the present invention has been described above in connection with several exemplary embodiments thereof, it would be apparent to those skilled in the art that those exemplary embodiments are provided solely for illustrating the present invention, and should not be relied upon to construe the appended claims in a limiting sense.

What is claimed is:

1. A radiotherapy apparatus controller comprising:
   a portal image taking unit configured to take a first transmission image, in which a marker member positioned at a predetermined position is shown, by using therapeutic radiation and an imager;
   a gantry position collector configured to collect a first gantry position at which a gantry is positioned when said first transmission image is taken from a sensor measuring a position at which said gantry is positioned, said gantry supporting said imager and a therapeutic radiation radiating device which radiates said therapeutic radiation;
   a marker position calculator configured to calculate a first marker position at which said marker member is shown in said first transmission image; and
   a marker position table generator configured to update a marker position table, which correlates a plurality of gantry positions with a plurality of marker positions, so that said first gantry position corresponds to said first marker position.

2. The radiotherapy apparatus controller according to claim 1, further comprising:
   a gap calculator configured to calculate a gap amount, base on a second transmission image taken by using said therapeutic radiation and said imager and a second marker position corresponding to a second gantry position at which said gantry is positioned when said second transmission image is taken in said plurality of marker positions; and
   a gimbal driver, with reference to a compensation table, which correlates said plurality of gantry positions and a plurality of gap amounts with a plurality of compensation amounts, configured to drive said therapeutic radiation radiating device against said gantry by using a driving unit based on a compensation amount corresponding to said second gantry position and said gap amount in said plurality of compensation amounts.

3. The radiotherapy apparatus controller according to claim 2, further comprising:
   an irradiation unit configured to vary a shape of an irradiation field of said therapeutic radiation by using an irradiation field varying unit, based on said second transmission image.

4. The radiotherapy apparatus controller according to claim 2, further comprising:
   an irradiation axis gap calculator configured to calculate an irradiation axis gap amount based on a third transmission image taken by using said therapeutic radiation and said imager; and
   a compensation table generator configured to update said compensation table based on said irradiation axis gap amount and a third gantry position at which said gantry is positioned when said third transmission image is taken.

5. The radiotherapy apparatus controller according to claim 1, wherein based on a fourth marker position corresponding to a fourth gantry position in said plurality of marker positions, said marker position table generator calculates a fifth marker position corresponding to a fifth gantry position different from said fourth gantry in said plurality of marker positions, and wherein said marker position table generator updates said marker position table so that said fifth gantry position corresponds to said fifth marker position.

6. The radiotherapy apparatus controller according to claim 1, further comprising:
a displaying unit configured to display a display image on a display, said display image indicating a marker position figure and a sixth transmission image taken by using said therapeutic radiation and said imager,
wherein said gantry position collector further collects a sixth gantry position at which said gantry is positioned when said sixth transmission image is taken,
wherein said marker position figure indicates a sixth marker position corresponding to said sixth gantry position in said plurality of marker positions.

7. An irradiation method, comprising:
taking a first transmission image, in which a marker member positioned at a predetermined position is shown, by using therapeutic radiation and an imager;
measuring a first gantry position at which a gantry is positioned when said first transmission image is taken, said gantry supporting said imager and a therapeutic radiation radiating device which radiates said therapeutic radiation;
calculating a first marker position at which said marker member is shown in said first transmission image; and
updating a marker position table, which correlates a plurality of gantry positions with a plurality of marker positions, so that said first gantry position corresponds to said first marker position.

8. The irradiation method according to claim 7, further comprising:
calculating a gap amount, base on a second transmission image taken by using said therapeutic radiation and said imager and a second marker position corresponding to a second gantry position at which said gantry is positioned when said second transmission image is taken in said plurality of marker positions; and
with reference to a compensation table, which correlates said plurality of gantry positions and a plurality of gap amounts with a plurality of compensation amounts, driving said therapeutic radiation radiating device against said gantry based on a compensation amount corresponding to said second gantry position and said gap amount in said plurality of compensation amounts.

9. The irradiation method according to claim 8, further comprising:
varying a shape of an irradiation field of said therapeutic radiation, based on said second transmission image.

10. The irradiation method according to claim 8, further comprising:
calculating an irradiation axis gap amount based on a third transmission image taken by using said therapeutic radiation and said imager; and
updating said compensation table based on said irradiation axis gap amount and a third gantry position at which said gantry is positioned when said third transmission image is taken.

11. The irradiation method according to claim 7, wherein said step of updating said marker position table, includes:
based on a fourth marker position corresponding to a fourth gantry position in said plurality of marker positions, calculating a fifth marker position corresponding to a fifth gantry position different from said fourth gantry in said plurality of marker positions, and
updating said marker position table so that said fifth gantry position corresponds to said fifth marker position.

12. The irradiation method according to claim 7, further comprising:
displaying a display image on a display, said display image indicating a marker position figure and a sixth transmission image taken by using said therapeutic radiation and said imager,
wherein said marker position figure indicates a sixth marker position corresponding to a sixth gantry position, at which said gantry is positioned when said sixth transmission image is taken, in said plurality of marker positions.

13. A computer-readable medium comprising code that, when executed, causes a computer to perform the following:
taking a first transmission image, in which a marker member positioned at a predetermined position is shown, by using therapeutic radiation and an imager;
collecting a first gantry position at which a gantry is positioned when said first transmission image is taken from a sensor measuring a position at which said gantry is positioned, said gantry supporting said imager and a therapeutic radiation radiating device which radiates said therapeutic radiation;
calculating a first marker position at which said marker member is shown in said first transmission image; and
updating a marker position table, which correlates a plurality of gantry positions with a plurality of marker positions, so that said first gantry position corresponds to said first marker position.

14. The computer-readable medium according to claim 13, further comprising:
calculating a gap amount, base on a second transmission image taken by using said therapeutic radiation and said imager and a second marker position corresponding to a second gantry position at which said gantry is positioned when said second transmission image is taken in said plurality of marker positions; and
with reference to a compensation table, which correlates said plurality of gantry positions and a plurality of gap amounts with a plurality of compensation amounts, driving said therapeutic radiation radiating device against said gantry by using a driving unit based on a compensation amount corresponding to said second gantry position and said gap amount in said plurality of compensation amounts.

15. The computer-readable medium according to claim 14, further comprising:
varying a shape of an irradiation field of said therapeutic radiation by using an irradiation field varying unit, based on said second transmission image.

16. The computer-readable medium according to claim 14, further comprising:
calculating an irradiation axis gap amount based on a third transmission image taken by using said therapeutic radiation and said imager; and
updating said compensation table based on said irradiation axis gap amount and a third gantry position at which said gantry is positioned when said third transmission image is taken.

17. The computer-readable medium according to claim 13, wherein said step of updating said marker position table, includes:
based on a fourth marker position corresponding to a fourth gantry position in said plurality of marker positions, calculating a fifth marker position corresponding to a fifth gantry position different from said fourth gantry in said plurality of marker positions, and updating said marker position table so that said fifth gantry position corresponds to said fifth marker position.

18. The computer-readable medium according to claim 13, further comprising:

displaying a display image on a display, said display image indicating a marker position figure and a sixth transmission image taken by using said therapeutic radiation and said imager, wherein said step of collecting said first gantry position, includes:

collecting a sixth gantry position at which said gantry is positioned when said sixth transmission image is taken, wherein said marker position figure indicates a sixth marker position corresponding to said sixth gantry position in said plurality of marker positions.

* * * * *